US008724935B2

(12) United States Patent
Arkwright et al.

(10) Patent No.: US 8,724,935 B2
(45) Date of Patent: May 13, 2014

(54) OPTICAL DEVICE

(75) Inventors: John William Arkwright, Campbell (AU); Ian Underhill, Eagle Heights (AU); Neil Blenman, Campbell (AU)

(73) Assignee: Commonwealth Scientific and Industrial Research Organisation, Campbell (AU)

( * ) Notice: Subject to any disclaimer, the term of this patent is extended or adjusted under 35 U.S.C. 154(b) by 737 days.

(21) Appl. No.: 12/922,001

(22) PCT Filed: Mar. 11, 2009

(86) PCT No.: PCT/AU2009/000287
§ 371 (c)(1),
(2), (4) Date: Dec. 13, 2010

(87) PCT Pub. No.: WO2009/111827
PCT Pub. Date: Sep. 17, 2009

(65) Prior Publication Data
US 2011/0116743 A1 May 19, 2011

(30) Foreign Application Priority Data

Mar. 11, 2008 (AU) ................................ 2008901137

(51) Int. Cl.
*G02B 6/00* (2006.01)
*G02B 6/34* (2006.01)
*G01J 1/04* (2006.01)
*G02B 6/124* (2006.01)
*G01D 5/353* (2006.01)
*G01L 1/24* (2006.01)

(52) U.S. Cl.
CPC .............. *G02B 6/124* (2013.01); *G01D 5/353* (2013.01); *G01L 1/243* (2013.01); *G01L 1/246* (2013.01); *G01L 1/247* (2013.01)
USPC ............. 385/13; 385/32; 385/37; 250/227.14

(58) Field of Classification Search
CPC ........ G02B 6/124; G01D 5/353; G01L 1/243; G01L 1/246; G01L 1/247
USPC .......... 385/12–14, 27, 32, 37–39; 250/227.14
See application file for complete search history.

(56) References Cited

U.S. PATENT DOCUMENTS

| 5,774,619 A | 6/1998 | Bruesselbach |
| 5,991,479 A * | 11/1999 | Kleinerman .................. 385/31 |
| 2004/0202401 A1 | 10/2004 | Berg et al. |

FOREIGN PATENT DOCUMENTS

| WO | 2005/083379 A1 | 9/2005 |
| WO | 2006/094353 A1 | 9/2006 |
| WO | 2007/000323 A1 | 1/2007 |
| WO | 2008/011663 A1 | 1/2008 |

OTHER PUBLICATIONS

Taher Omari, et al., "Manometry in the 21st Century: A Novel Fibre Optic Based Technology for Multi-Channel Intraluminal Manometry", American Journal of Gastroenterology, 2006, vol. 130, A730.

* cited by examiner

*Primary Examiner* — Uyen Chau N Le
*Assistant Examiner* — Michael Mooney
(74) *Attorney, Agent, or Firm* — Sughrue Mion, PLLC

(57) ABSTRACT

The present disclosure provides an optical device comprising a first optical fiber portion having a first region and further regions between which the first region is positioned. The optical device also comprises a second optical fiber portion having a second region and further regions between which the second region is positioned. Further, the optical fiber comprises at least one member to which the first and second optical fiber portions are attached at the first and second regions. The first and second regions are positioned at opposite sides of an area defined between the first and second regions and spaced apart from each other by a first distance and wherein adjacent further regions are spaced apart by a second distance that is smaller than the first distance.

16 Claims, 3 Drawing Sheets

OPTICAL DEVICE

FIELD OF THE INVENTION

The present invention broadly relates to an optical device and relates specifically, though not exclusively, to an optical device for sensing a property.

BACKGROUND OF THE INVENTION

Optical devices are widely used for sensing different properties. Such optical devices may comprise optical fibres that have sensing regions in which a change in a property causes a change in an optical condition for guiding light in the optical fibres.

For example, an optical device may be arranged for sensing changes in temperature, strain or pressure and may comprise a Bragg grating which has an optical response that depends on the strain of the Bragg grating. A change in an external pressure or temperature may cause a change in strain of the Bragg grating, which in turn causes a change in a light interference condition. Consequently, the change in external pressure or temperature can be detected by monitoring an optical response of the Bragg grating.

The optical device may comprise any number of optical fibres with or without Bragg gratings. For example the optical device may comprise a pair of optical fibres. One optical fibre may be arranged for sensing a first property and another property may be arranged for sensing a second property. However, such optical devices having a pair of optical fibres have the disadvantage that mechanical bending flexibility of the device is reduced in a plane in which the optical fibres are positioned.

There is a need for technological advancement.

SUMMARY OF THE INVENTION

The present invention provides in a first aspect an optical device comprising:
  a first optical fibre portion having a first region and further regions between which the first region is positioned;
  a second optical fibre portion having a second region and further regions between which the second region is positioned; and
  at least one member to which the first and second optical fibre portions are attached at the first and second regions;
  wherein the first and second regions are positioned at opposite sides of an area defined between the first and second regions and spaced apart from each other by a first distance and wherein adjacent further regions are spaced apart by a second distance that is smaller than the first distance.

The first region may be a first sensing region for sensing a first property. The second region may be a second sensing region for sensing a second property.

The first optical fibre portion may be attached to the at least one member at attachment regions between which the first sensing region is defined. The second optical fibre portion may be attached to the at least one member at attachment regions between which the second sensing region is defined.

The at least one member typically is a rigid member.

As the adjacent further regions are spaced apart by a second distance that is smaller then the first distance, the optical device typically has, at the further regions, a bending flexibility that is locally increased compared with the bending flexibility that a device would have in a plane if the optical fibre portions were positioned parallel to each other in that plane.

In one specific embodiment the optical device comprises a region in which the distance between the first and second optical fibre portions is decreasing until the optical fibre portions are positioned adjacent each other, typically immediately adjacent each other, or crossing each other. In this case, especially when the first and second regions are positioned close to one another, the bending flexibility of the optical device is particularly increased.

The optical device may be arranged for sensing any type of property, such as pressure, strain or temperature. The optical device may be arranged so that the first and the second properties are the same properties. Alternatively, the optical device may be arranged so that the first and the second properties are different properties. Further, the optical device may be arranged for sensing any number of properties. In another variation the optical device may not be arranged for sensing a property or only one of the first and second optical fibre portions may comprise a sensing region for sensing a property.

The first and second optical fibre portions may be portions of two separate optical fibres.

The first optical fibre portion may be one of a plurality of first optical fibre portions. Further, the second optical fibre portion may be one of a plurality of second optical fibre portions. In one example the first and second optical fibre portions are portions of a continuous length of fibre having been folded so that the first region is juxtaposed to the second region.

In one specific embodiment the first and second optical fibre portions comprise a plurality of the first and second regions. In this case the device typically is arranged so that at least one of the further regions is positioned between adjacent ones of the first regions and at least one of the further regions is positioned between adjacent ones of the second regions. For example, in a direction from one of the first regions to an adjacent first region the distance between the first and second optical fibre portions may first decrease and then increase again.

The optical device may be arranged so that one of the first and second optical fibre portions passes over another one of the first and second optical fibre portions at more than one position between adjacent first regions and between adjacent second regions.

Alternatively, the device may also be arranged so that the distance between the first and the second optical fibre portions has a minimum at a position between adjacent first regions, but the first and second optical fibre portions do not pass over one another.

The present invention provides in a second aspect an optical device comprising:
  a first optical fibre portion having a first region;
  a second optical fibre portion having a second region, the second region being located at a position that is juxtaposed to that of the first region;
  at least one member to which the first and second optical fibre portion are attached at the first and second regions;
  an optical fibre portion having a further region distant from the first region;
  wherein the device is arranged so that in use signals from both the first and the second regions of the first and second optical fibre portions, respectively, are guided through the further region.

The device typically is arranged so that, because both signals typically are guided through the same optical fibre portion at the further region, the bending flexibility of the device is increased at the further region.

The first region typically is a first sensing region for sensing a first property. The second region may be a second sensing region for sensing a second property.

The first optical fibre portion may be attached to the at least one member at attachment regions between which the first sensing region is defined. The second optical fibre portion may be attached to the at least one member at attachment regions between which the second sensing region is defined.

The at least one member typically is a rigid member.

The optical device may comprise one optical fibre that comprises the first and second optical fibre portions and which is bent so that the first region is juxtaposed to the second region. For example, the optical fibre may be bent so that a U or S-shaped section is formed.

Alternatively, the first and the second optical fibre portions may be coupled at end-portions to an end-portion of a further optical fibre portion. For example, the coupling may be performed using an optical y-coupler.

In one specific embodiment of the present invention the first and second optical fibre portions comprise a plurality of first and second regions, respectively, and a plurality of the further regions. In this case the optical device typically is arranged so that at least one of the further regions is positioned between adjacent ones of the first sensing regions.

The sections that follow hereafter will describe features that relate to the optical device according to the first and second aspect of the present invention.

The first and second regions may locally be bent away from each other so that a convexly shaped area is defined between the first and second regions.

At least one of the first and second sensing regions typically comprises a sensing device such as a Bragg grating that is arranged so that a change in a suitable property causes a change in strain of the Bragg grating and can be detected by detecting a change in an optical response of the Bragg grating. The at least one first sensing region may comprise a first Bragg grating and the at least one second sensing region may comprise a second Bragg grating. Alternatively, the at least one of the first and second sensing regions may comprise any other suitable type of sensing device, such as a surface plasmon resonance sensor.

The optical device may comprise an external catheter that may be arranged for insertion into a human body. Further, the optical device may comprise a portion comprising an X-ray opaque material which enables imaging the position of the device in the human body.

The optical device may comprise a plurality of the members, which typically are rigid members.

In one specific embodiment the optical device is arranged for pressure sensing and comprises:
 a first Bragg grating incorporated in the first sensing region;
 a second Bragg grating incorporated in the second sensing region; and
 a moveable wall portion coupled to the first Bragg grating so that a movement of the moveable wall portion causes a force that effects a change in strain of the first Bragg grating and thereby effects a change in an optical period of the first Bragg grating.

The first optical fibre portion may be one of a plurality of first optical fibre portions and the moveable wall portion may be one of a plurality of moveable wall portions to which the first optical fibre portions are coupled. In this embodiment the optical device typically comprises a plurality of rigid members defining the sensing regions between attachment regions and the attachment regions typically are arranged so that axial forces acting on the optical device at a position distant from the sensing regions do not affect the optical response of the first and second Bragg gratings.

The optical device in accordance with the specific embodiment of the present invention typically is arranged so that the force caused by a change in external pressure is a sideway-force on the at least one first Bragg grating. The optical device may be used for pressure sensing in any environment, including for example in-vivo environments, laboratories and wind tunnels.

At least some of the optical fibre portions may be bent at the sensing regions. For example, the at least one first and at least one second sensing region may be bent away from each other, and are typically curved, so that a convexly shaped area is defined between the at least one first and the at least one second optical fibre portions. Since the optical fibre portions are curved, the sensitivity of the at least one first Bragg grating to respond to a change in external force with a change in strain typically is increased.

In this embodiment the at least one second Bragg grating may be positioned so that a movement of a respective moveable wall portion will not effect a change in strain of the each second Bragg grating. The at least one second Bragg grating typically is arranged so that it will experience substantially only a change in optical response in response to a change in temperature whereby the optical device is arranged so that the change in optical response of the second Bragg grating can be used to correct a detected change in optical response of the first Bragg grating for an influence of the change in temperature.

The invention will be more fully understood from the following description of specific embodiments of the invention. The description is provided with reference to the accompanying drawings.

DETAILED DESCRIPTION OF SPECIFIC EMBODIMENTS

An optical device according to embodiments of the present invention is now described. In the described embodiment the optical device is arranged for pressure sensing. However, it is to be appreciated by a person skilled in the art that the device may alternatively be arranged for sensing any other properties, such as temperature or strain. Further, the device may be arranged for sensing any number of suitable properties, which may or may not be the same properties. In addition, the optical device may not be arranged for sensing a property.

Figure 1:
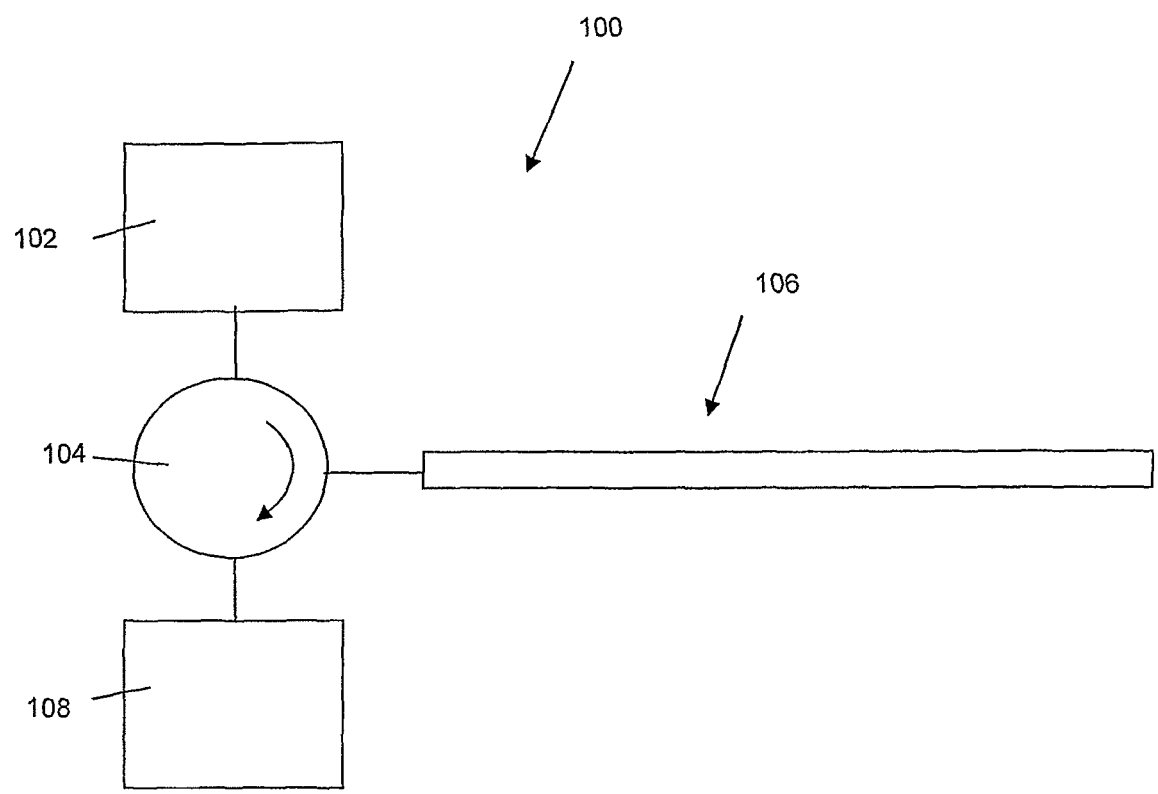
FIG. 1 shows an optical system according to a specific embodiment of the present invention.

Referring initially to FIG. 1, a system for pressure sensing is now described. The system 100 comprises a light source 102 which in this embodiment is a broadband light source commonly referred to as a "white" light source even though the light that is emitted by the light source 102 may have any continuous wavelength range. The light is directed via optical circulator 104 to a device for pressure sensing 106. In a variation of this embodiment the circulator 104 may be replaced by an optical coupler, an optical splitter or an optical beam splitter.

The device 106 may comprise a catheter for insertion into the human body. Further, the device 106 typically comprises an X-ray opaque material or series of x-ray opaque elements, such as a metallic material, for locating the device 106 in the human body.

In this embodiment the device 106 comprises a plurality of Bragg gratings (not shown) which are formed in one or more optical fibres. The Bragg gratings of a first group are arranged so that a change in external pressure results in a change in strain of one or more of the Bragg gratings of the first group. The change in strain causes a change in an optical period of the at least one Bragg grating of the first group, which is detectable by detecting an optical response.

All Bragg gratings also experience a change in strain in response to a change in temperature. Bragg gratings of a second group of the Bragg gratings are positioned so that a change in external pressure does not result in a change in the optical period which is only affected by a change in temperature. Comparing the responses of Bragg gratings of the first group with that of Bragg gratings of the second group allows obtaining information on changes in the external pressures that is corrected for influences of changes in temperature.

The light that is produced by the light source 102 and that is directed to the Bragg gratings causes responses from the Bragg gratings which are directed via the optical circulator 104 to optical analyser 108 for optical analysis. Such a procedure is commonly referred to as wavelength division multiplexing. The Bragg gratings may also effect optical responses which overlap in wavelength or frequency space as long as sufficient information is known about each Bragg grating to allow the signals to be successfully deconvolved.

Figure 2:
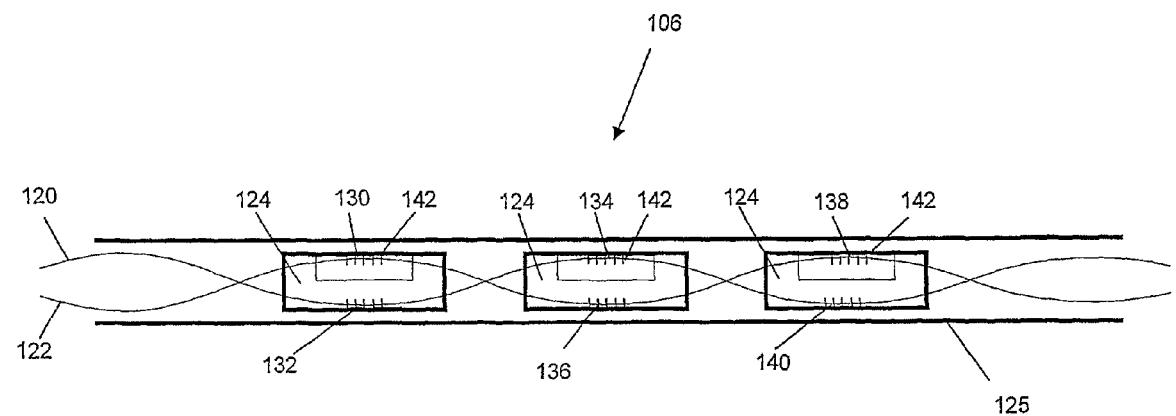
FIG. 2 shows an optical device according to an embodiment of the present invention.

FIG. 2 shows the device 106 in more detail. The device 106 comprises in this example optical fibres 120 and 122, rigid members 124 and an outer sheath 125. The optical fibres 122 and 120 comprise Bragg gratings 130, 132, 134, 136, 138, and 140. Each rigid member 124 has a movable wall portion which is provided in the form of a diaphragm 142. In this embodiment, the optical fibres 120 and 122 are rigidly connected at attachment regions to respective rigid members 124 so that each Bragg grating 130, 132, 134, 136, 138, and 140 is positioned between two immediately adjacent attachment regions.

The Bragg gratings 130, 134 and 138 are positioned at a window of a respective rigid member 124 and on, in or near a respective diaphragm 142 such that an external pressure change effects movement of the diaphragm which in turn causes a change in strain of the respective Bragg grating 130, 134 or 138. The change in strain causes a change of an optical property of the Bragg gratings 130, 134 or 138, such as a change of an optical path length, which influences optical responses of the Bragg gratings 130, 134 and 138.

The Bragg gratings 132, 136 and 140 are positioned so that a change in external pressure will not cause a change in optical response of the Bragg gratings and these Bragg gratings are provided in order to detect local changes in strain that are a result of local changes in temperature. Detected changes in strain of the Bragg gratings 132, 136 and 140 may be used to correct detected changes in strain of the Bragg gratings 130, 134 and 138 for a direct impact of a temperature change on the strain and for an indirect impact by a temperature induced change in elasticity of the diaphragm (using an empirically determined factor that characterises the change in elasticity of the diaphragm as a function of temperature in first order).

In this example the device 106 is arranged so that each optical fibre comprises Bragg gratings that are exposed to forces resulting from changes in external pressures and Bragg gratings that only experience a change in strain in response to a change in temperature. For example, the optical fibre 120 comprises the Bragg grating 134 that is exposed to external forces and the Bragg gratings 132 and 140 that are not exposed to external forces. In this embodiment the analyser 108 is arranged so that the responses of the Bragg gratings 130, 134 and 138 are compared with those of the Bragg gratings 132, 136 and 140, respectively.

In this embodiment the optical fibres 120 and 122 are bent so that the optical fibres pass over one another and the rigid members 124 are positioned between locations at which the optical fibres 120 and 122 pass over one another. Because of this particular arrangement of the optical fibres 120 and 122, the mechanical flexibility of the device 106 at the locations at which the optical fibres pass over one another is significantly increased compared to the case of a device comprising two straight and parallel optical fibres. In variations of the described embodiment the optical fibres may not necessarily pass over one another, but may be bent so that a distance between the optical fibres has minima. Further variations will be described below with reference to FIG. 3.

The rigid members 124 are formed from a rigid material, such as silicon, a plastics or metallic material (for example stainless steel, invar, tungsten, or kovar), or any other suitable rigid material. In this embodiment the device 106 comprises six Bragg gratings. In alternative embodiments the device 106 may comprise any other number of Bragg gratings at any fixed or variable pitch. Further it is to be appreciated by a skilled person that each optical fibre 120 and 122 may only comprise one Bragg grating. In addition, the device 106 may only comprise one rigid member and the Bragg gratings of the optical fibres 120 and 122 may both be attached to that rigid member. The device 106 may also comprise more than two optical fibres with Bragg gratings.

In this embodiment the Bragg gratings 130, 134 138 and 132, 136, 140 have a slightly different refractive index variation so that each Bragg grating has an optical response that has a slightly different spectral response.

As in this embodiment each Bragg grating 130, 134 and 138 causes a different response, it is possible to associate a particular response with a position along the device 106. Consequently, it is possible to perform distributed pressure measurements and detect relative pressure difference between the positions of the Bragg gratings 130, 134 and 138. The combined response from the Bragg gratings is wavelength division multiplexed and the optical analyser 108 uses known wavelength division de-multiplexing techniques to identify the responses from the respective grating positions. Suitable software routines are used to determine a pressure or pressure distribution from the optical responses received from the Bragg gratings. Pressure measurements typically include calibrating the device.

In a variation of this embodiment at least some of the Bragg gratings may be identical and consequently, if the strain conditions are the same, their optical response will also be the same. In this case a pulsed light source may be used to guide light to the Bragg gratings and the positions of the Bragg gratings may be estimated from a time at which the responses are received by the optical analyser 108. Alternatively, a frequency component dependent on the location of each grating may be used to first identify the position of the grating or sensor being interrogated.

The rigid members 124 together with the diaphragms 142 may each define a closed interior space in which for example two of the Bragg gratings may be located. Alternatively, the rigid members 124 may comprise openings so that the internal spaces of the rigid members are in fluidal communication with each other.

Figure 3:
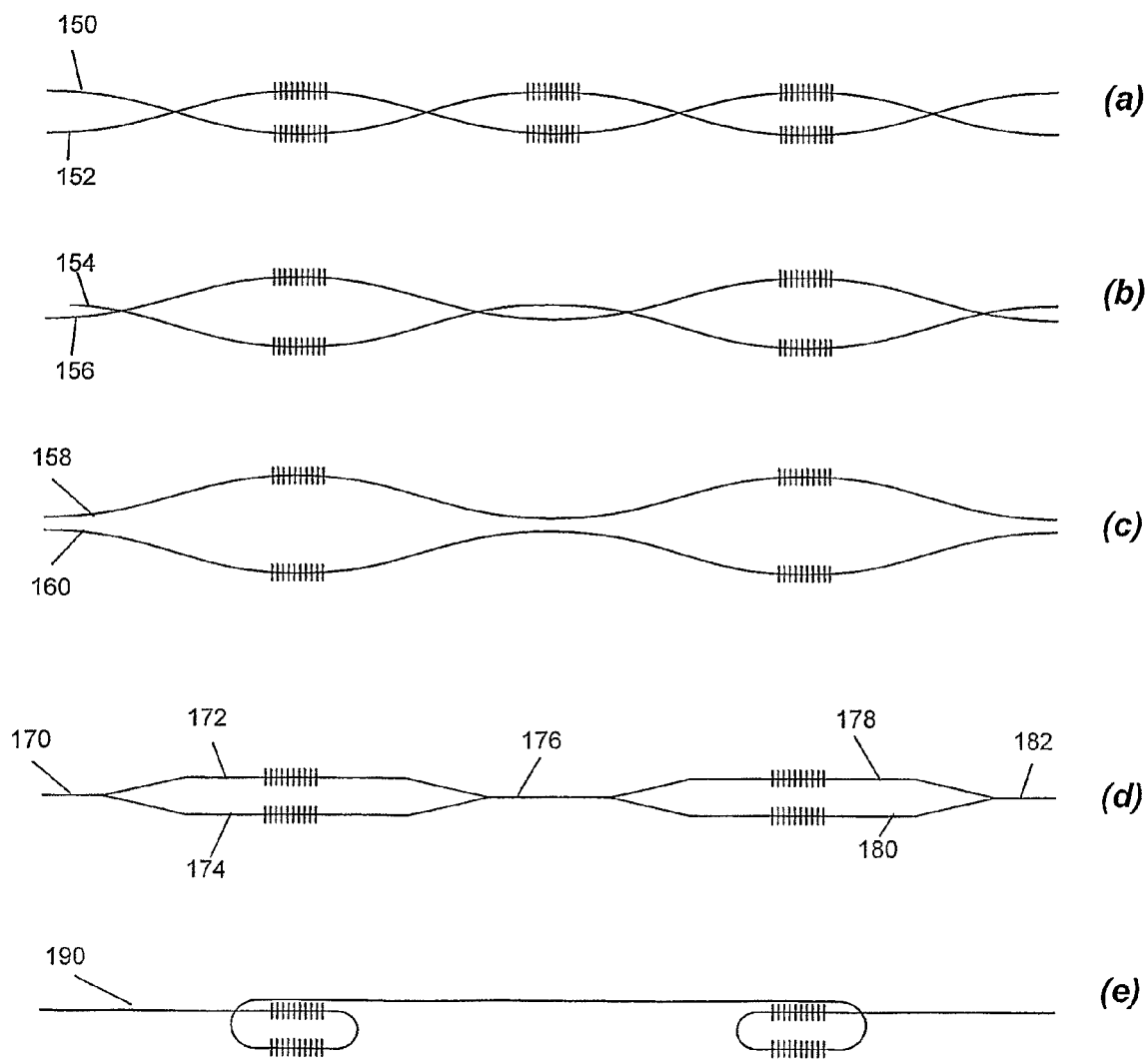
FIG. 3 (*a*)-(*e*) show components of an optical device according to embodiments of the present invention.

Referring to FIG. 3, further variations of a device for pressure sensing in accordance with embodiments of the present invention are now described. FIG. 3 (a) to (c) shows pairs of optical fibres with Bragg gratings and which may replace the optical fibres 120 and 122 shown in FIG. 2.

FIG. 3 (a) shows optical fibres 150 and 152 which are arranged in the same manner as the optical fibres 120 and 122 shown in FIG. 2. FIG. 3 (b) shows another variation in which optical fibres 154 and 156 pass over one another at two locations between the locations of the Bragg gratings. FIG. 3 (c) shows a further variation in which optical fibres 158 and 160 do not pass over one another, but are arranged so that the distance relative to each other has a minimum between the locations of the Bragg gratings. FIGS. 3 (b) and (c) shows examples in which one of the optical fibres only comprises Bragg gratings that are exposed to external forces caused by changes in external pressures and the other one of the optical fibres only comprises Bragg gratings that are arranged to monitor a change in temperature.

A person skilled in the art will appreciate that also combinations of the shown variations are within the scope of embodiment of the present invention. For example, the optical fibres may pass over one another at any number of locations and may also be arranged so that at other locations the distance between the optical fibres is reduced without passing over of the optical fibres at these other locations.

FIG. 3 (d) shows another variation of a device for pressure measurement in accordance with an embodiment of the present invention. In this example the device comprises an optical fibre portion 170 that is coupled to optical fibre portions 172 and 174 via an optical y-coupler. The optical fibre portions 172 and 174 comprise Bragg gratings and are coupled to optical fibre portion 176 via a further optical y-coupler. Further, the device comprises optical fibre portions 178 and 180 with Bragg gratings and which re coupled to the optical fibre portion 176 and 182 via additional optical y-couplers. In this embodiment the device has regions that comprise single optical fibre portions (optical fibre portions 170, 176 and 182), and consequently has a relatively large flexibility at these regions.

The Bragg gratings of the optical fibre portions 172, 174, 178 and 180 may be located in two rigid members, such as rigid members 124 with diaphragms 142 shown in FIG. 2, so that Bragg gratings of the optical fibre portions 172 and 178 are exposed to forces resulting from changes in external pressures and the Bragg gratings of the optical fibre portions 174 and 180 are only exposed to changes in strain resulting from temperature changes.

FIG. 3 (e) shows a further variation of the device for pressure sensing according to an embodiment of the present invention. Optical fibre 190 comprises in this embodiment four Bragg gratings and is bent such that the optical fibre comprises pairs of substantially parallel Bragg gratings. The pairs of the Bragg gratings may be located in respective rigid members, such as rigid members 124 with diaphragms shown in FIG. 2, so that one Bragg grating of each pair is exposed to forces resulting from changes in external pressures and the other one is only exposed to changes in strain resulting from temperature changes. In this embodiment the device comprises a single optical fibre and consequently has a relatively large flexibility.

Although the invention has been described with reference to particular examples, it will be appreciated by those skilled in the art that the invention may be embodied in many other forms. As mentioned above, the device may be arranged for sensing any other suitable property and may comprise any number of optical fibre portions for sensing the properties at sensing regions, which may or may not comprise Bragg gratings.

The invention claimed is:

1. An optical device comprising:
   a first optical fibre portion having a first sensing region and further regions between which the first sensing region is positioned;
   a first Bragg grating incorporated in a first sensing region;
   a second optical fibre portion having a second sensing region and further regions between which the second sensing region is positioned;
   a second Bragg grating incorporated in a second sensing region;
   at least one member to which the first and second optical fibre portions are attached at the first and second sensing regions;
   a moveable wall portion coupled to the first Bragg grating so that a movement of the moveable wall portion causes a force that effects a change in strain of the first Bragg grating and thereby effects a change in an optical period of the first Bragg grating whereby the optical device is arranged for pressure sensing; and
   wherein the first and second sensing regions are positioned at opposite sides of an area defined between the first and second sensing regions and spaced apart from each other by a first distance and wherein adjacent further regions are spaced apart by a second distance that is smaller than the first distance.

2. The optical device of claim 1 wherein the first optical fibre portion is attached to the at least one member at attachment regions between which the first sensing region is defined.

3. The optical device of claim 1, wherein the second optical fibre portion is attached to the at least one member at attachment regions between which the second sensing region is defined.

4. The optical device of claim 1 wherein the at least one member is a rigid member.

5. The optical device of claim 1 wherein the first and the second sensing regions are arranged for sensing the same properties.

6. The optical device of claim 1 wherein the optical device is arranged so that the first and the second properties are different properties.

7. The optical device of claim 1 comprising a plurality of the first and second regions.

8. An optical device comprising:
   a first optical fibre portion having a first sensing region;
   a first Bragg grating incorporated in the first sensing region;
   a second optical fibre portion having a second sensing region, the second region being located at a position that is juxtaposed to that of the first sensing region;
   a second Bragg grating incorporated in the second sensing region;
   at least one member to which the first and second optical fibre portions are attached at the first and second sensing regions;
   an optical fibre portion having a further region distant from the first region;
   a moveable wall portion coupled to the first Bragg grating so that a movement of the moveable wall portion causes a force that effects a change in strain of the first Bragg grating and thereby effects a change in an optical period of the first Bragg grating whereby the optical device is arranged for pressure sensing; and wherein the device is arranged so that in use signals from both the first and the second sensing regions of the first and second optical fibre portions, respectively, are guided through the further region.

9. The optical device of claim 8 wherein the first optical fibre portion is attached to the at least one member at attachment regions between which the first sensing region is defined.

10. The optical device of claim 9 wherein the second optical fibre portion is attached to the at least one member at attachment regions between which the second sensing region is defined.

11. The optical device of claim 8 wherein the at least one member is a rigid member.

12. The optical device of claim 8 comprising one optical fibre that comprises the first and second optical fibre portions and which is bent so that the first region is juxtaposed the second region.

13. The optical device of claim 8 wherein the first and the second optical fibre portions are coupled at end-portions to an end-portion of a further optical fibre portion.

14. The optical device of claim 5 wherein the first optical fibre portion is one of a plurality of first optical fibre portions and the moveable wall portion is one of a plurality of moveable wall portions to which the first optical fibre portions are coupled and wherein the optical device comprises a plurality of rigid members defining the sensing regions between attachment regions and the attachment regions.

15. The optical device of claim 8 wherein the optical device is arranged so that the force caused by a change in external pressure is a sideway-force on the at least one first Bragg grating.

16. The optical device of claim 8 wherein the at least one second Bragg grating is arranged so that it will experience substantially only a change in strain in response to a change in temperature whereby the optical device is arranged so that the change in strain of the second Bragg grating can be used to correct a detected change in strain of the first Bragg grating for an influence of the change in temperature.

* * * * *